United States Patent [19]

Coran et al.

[11] 3,974,163
[45] Aug. 10, 1976

[54] POLY(THIOMAIDES)

[75] Inventors: Aubert Yaucher Coran; Joseph Edward Kerwood, both of Akron, Ohio

[73] Assignee: Monsanto Company, St. Louis, Mo.

[22] Filed: June 25, 1973

[21] Appl. No.: 373,134

Related U.S. Application Data

[60] Division of Ser. No. 113,633, Feb. 8, 1971, Pat. No. 3,775,428, which is a continuation-in-part of Ser. No. 80,815, Oct. 14, 1970, abandoned, which is a continuation-in-part of Ser. No. 704,186, Sept. 20, 1967, abandoned, which is a division of Ser. No. 646,202, June 15, 1967, abandoned, which is a continuation-in-part of Ser. No. 579,493, Sept. 15, 1966, abandoned, and a continuation-in-part of Ser. No. 549,730, May 12, 1966, abandoned, and a continuation-in-part of Ser. No. 459,466, May 27, 1965, abandoned, said Ser. No. 80,815, is a division of Ser. No. 704,186, Sept. 20, 1967, abandoned.

[52] U.S. Cl. .................. 260/281 GP; 260/239 A; 260/281 S; 260/239.3 R; 260/293.63; 260/293.64; 260/306; 260/309.2; 260/309.7; 260/309.5; 260/326 S; 260/326.26; 260/553 A; 260/553 R; 260/558 S; 260/561 S; 260/326 C; 260/780

[51] Int. Cl.² .............. C07D 211/96; C07D 207/48; C07D 223/10; C07D 225/02

[58] Field of Search ................ 260/326.26, , 326 S, 260/281, 239.3 R, 780, 789, 281 GF

[56] References Cited
UNITED STATES PATENTS 3,546,185  12/1970  Coran .............................. 260/79.5

3,709,907  1/1973  Behforouz ..................... 260/326 S
3,872,062  3/1975  Lawrence ...................... 260/79.5 B

OTHER PUBLICATIONS

Kirk–Othmer, Encyclopedia of Chemical Tech. 7, 793.
Behforouz et al., J. Org. Chem., 34, p. 53 (1969).

*Primary Examiner*—Alton D. Rollins
*Assistant Examiner*—Mark L. Berch

[57] ABSTRACT

New compounds with a nucleus of

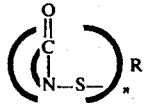

where $n$ is 2 to 4 and

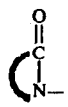

is a radical derived by removal of hydrogen from an imide of an acyclic dicarboxylic acid, from a monocarbonyl cyclic urea, from an imide in which nitrogen is linked to carbonyl by alkylene and from a monocarbonyl azole containing one other different hetero atom in the ring. R is alkylene, arylene, cycloalkylene, or residue from ester of mercapto lower fatty acid and polyhydric alcohol which compounds are inhibitors of premature vulcanization of diene rubbers.

12 Claims, No Drawings

POLY(THIOMAIDES)

CROSS REFERENCE TO RELATED APPLICATIONS

This application is a division of application Ser. No. 113,633 filed Feb. 8, 1971 now U.S. Pat. No. 3,775,428 issued Nov. 27, 1973 which is a continuation-in-part of application Ser. No. 80,815 filed Oct. 14, 1970 now abandoned. Ser. No. 113,633 also is a continuation-in-part of application Ser. No. 704,186 filed Sept. 20, 1967, now abandoned, which is a division of application Ser. No. 646,202 filed June 15, 1967, now abandoned which is a continuation-in-part of the copending application Ser. No. 579,493 filed Sept. 15, 1966, now abandoned, a continuation-in-part of the copending application Ser. No. 549,730 filed May 12, 1966, now abandoned, and a continuation-in-part of the copending application Ser. No. 459,466 filed May 27, 1965, now abandoned. Said Ser. No. 80,815 filed Oct. 14, 1970 is a division of said Ser. No. 704,186 filed Sept. 20, 1967. The aforesaid prior applications are incorporated herein by reference.

BACKGROUND OF THE INVENTION

The invention pertains to the field of controlled-rubber vulcanization art. The applicable U.S. patent classification defines the invention as "retarders."

In the manufacture of vulcanized rubber products, crude rubber is combined with various other ingredients such as fillers, accelerators, and antidegradants to alter and improve processing of the rubber and to improve the properties of the final product. The crude rubber is put through several steps in the plant before it is ready for the final step of vulcanization. Generally, the rubber is mixed with carbon black and other ingredients except the vulcanizing agent and accelerator. Then the vulcanizing and accelerating agents are added to this masterbatch in a Banbury mixer or a mill. Scorching, viz., premature vulcanization, can occur at this stage of the processing, during the storage period before vulcanizing, and during the actual vulcanization. After the vulcanizing and accelerating agents are added, the mixture of crude rubber is ready for calendering or extruding and vulcanization. If premature vulcanization occurs during the storage of the crude mixture or during processing prior to vulcanization, the processing operations cannot be carried out because the scorched rubber is rough and lumpy, consequently, useless. Premature vulcanization is a major problem in the rubber industry and must be prevented in order to allow the rubber mix to be preformed and shaped before it is cured or vulcanized.

There are several reasons offered for premature vulcanization. The discovery of the thiazolesulfenamide accelerators constituted a major breakthrough in the vulcanization art, because thiazolesulfenamides delayed onset of the vulcanizing process; but, once it started, the built-in amine activation of the thiazole resulted in strong, rapid curing. Mercaptobenzothiazole is a valuable organic vulcanization accelerator but by present standards would be considered scorchy. It has been largely replaced by the delayed-action accelerators. The development of high pH furnace blacks which lack the inherent inhibiting effect of the acidic channel blacks and popularity of certain phenylenediamine antidegradants which promote scorching have placed increasingly stringent demands on the accelerator system.

Retarders have long been available to rubber compounders. These include N-nitrosodiphenylamine, salicylic acid, and a terpene-resin acid blend. See Editors of *Rubber World*, "Compounding Ingredients for Rubber," 125-128 (3rd. Ed., 1965). Acids as retarders are generally ineffective with thiazolesulfenamide accelerators or adversely affect this vulcanizing process. Nitrosoamines as retarders are only of limited effectiveness with thiazolesulfenamides derived from primary amines.

SUMMARY

We have discovered a class of sulfenimides which are extremely valuable inhibitors of premature vulcanization. The characteristic nucleus is

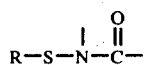

where the dangling valence on the nitrogen is linked to a second carbonyl and R is alkyl, aryl, or cycloalkyl. Aryl is used in the usual generic sense to mean any univalent organic radical where free valence belongs to an aromatic carbocyclic nucleus and not to a side chain. The term includes radicals substituted in the carbocyclic nucleus, for example, by alkyl, alkoxy, nitro, chloro, bromo, fluoro, iodo, and hydroxy. Alkyl is used in the usual generic sense to mean univalent aliphatic radicals of the series $C_nH_{2n+1}$. Primary, secondary, and tertiary alkyls are included, for example, straight or branched chains. The term cycloalkyl includes cycloalkyl radicals of 5 to 8 carbon atoms in the ring. The R may be substituted to give a bis-sulfenimide of the formula R'—S—R—S—R' where R is an alkane, arylene, or cycloalkane and R' is an imide. A combination of an accelerator and an inhibitor of this invention is an improved rubber additive which allows longer and safer processing time.

DESCRIPTION OF THE PREFERRED EMBODIMENTS

Our invention is that bis-sulfenimides having the formula

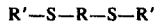

are excellent premature vulcanization inhibitors for a vulcanizable diene rubber where R is an alkane, arylene, or cycloalkane, and R' is an imide. Examples of the compounds useful in this invention are as follows: 1,1-bis(2-thiophthalimido)methane, 1,2-bis(2-thiophthalimido)ethane, 1,3-bis(2-thiophthalimido)propane, 1,2-bis)2-thiophthalimido)isopropane, 1,4-bis(2-thiophthalimido)butane, 1,1-bis(N-thio-5,5-dimethylhydantoin)methane, 1,2-bis(N-thio-5,5-dimethylhydantoin)ethane, 1,3-bis(N-thio-5,5-dimethylhydantoin)propane, 1,2-bis(N-thio-5,5-dimethylhydantoin)isopropane, 1,4-bis(N-thio-5,5-dimethylhydantoin)butane, 1,3-bis(N-thio-5,5-dimethylhydantoin)isobutane, 1,5-bis(N-thio-5,5-dimethylhydantoin)pentane, 1,6-bis(N-thio-5,5-dimethylhydantoin)hexane, 1,7-bis(N-thio-5,5-dimethylhydantoin)heptane, 1,8-bis(N-thio-5,5-dimethylhydantoin)octane, 1,4-bis(N-thio-5,5-dimethylhydantoin)cyclohexane, 1,4-bis(N-thio- 5,5-dimethylhydantoin)benzene, 1,4-bis(N-thio-5,5-dimethylhydantoin)nitrobenzene, 1,4-bis(N-thio-5,5-dimethylhydantoin)toluene, 1,1-bis(N-thiohexahydrophthalimido)methane, 1,2-bis(N-thiohexahydrophthalimido)ethane, 1,3-bis(N-thiohexahydrophthalimido)propane, 1,2-bis(N-thiohexahydrophthalimido)isopropane, 1,4-bis(N-thiohexahydrophthalimido)butane,
1,3-bis(N-thiohexahydrophthalimido)isobutane
1,5-bis(N-thiohexahydrophthalimido)pentane
1,6-bis(N-thiohexahydrophthalimido)hexane
1,7-bis(N-thiohexahydrophthalimido)heptane
1,8-bis(N-thiohexahydrophthalimido)octane
1,4-bis(N-thiohexahydrophthalimido)cyclohexane
1,4-bis(N-thiohexahydrophthalimido)benzene
1,4-bis(N-thiohexahydrophthalimido)nitrobenzene
1,4-bis(N-thiohexahydrophthalimido)toluene
1,6-bis(2-thiosuccinimido)hexane
1,7-bis(2-thiosuccinimido)heptane
1,8-bis(2-thiosuccinimido)octane
1,4-bis(2-thiosuccinimido)cyclohexane
1,4-bis(2-thiosuccinimido)benzene
1,4-bis(2-thiosuccinimido)nitrobenzene
1,4-bis(2-thiosuccinimido)toluene
1,1-bis(2-thioglutarimido)methane
1,2-bis(2-thioglutarimido)ethane
1,3-bis(2-thioglutarimido)propane
1,2-bis(2-thioglutarimido)isopropane
1,4-bis(2-thioglutarimido)butane
1,3-bis(2-thioglutarimido)-3-isobutane
1,5-bis(2-thioglutarimido)pentane
1,6-bis(2-thioglutarimido)hexane
1,7-bis(2-thioglutarimido)heptane
1,8-bis(2-thioglutarimido)octane
1,4-bis(2-thioglutarimido)cyclohexane
1,4-bis(2-thioglutarimido)benzene
1,4-bis(2-thioglutarimido)nitrobenzene
1,4-bis(2-thioglutarimido)toluene
1,1-bis(2-thiomaleimido)methane
1,2-bis(2-thiomaleimido)ethane
1,3-bis(2-thiomaleimido)propane
1,2-bis(2-thiomaleimido)isopropane
1,4-bis(2-thiomaleimido)butane
1,3-bis(2-thiomaleimido)-3-isobutane
1,5-bis(2-thiomaleimido)pentane
1,6-bis(2-thiomaleimido)hexane
1,7-bis(2-thiomaleimido)heptane
1,8-bis(2-thiomaleimido)octane
1,4-bis(2-thiomaleimido)cyclohexane
1,4-bis(2-thiomaleimido)benzene
1,4-bis(2-thiomaleimido)nitrobenzene
1,4-bis(2-thiomaleimido)toluene
1,1-bis(2-thionaphthalimido)methane
1,2-bis(2-thionaphthalimido)ethane
1,3-bis(2-thionaphthalimido)propane
1,2-bis(2-thionaphthalimido)isopropane
1,4-bis(2-thionaphthalimido)butane
1,3-bis(2-thionaphthalimido)-3-isobutane
1,5-bis(2-thionaphthalimido)pentane
1,6-bis(2-thionaphthalimido)hexane
1,7-bis(2-thionaphthalimido)heptane
1,8-bis(2-thionaphthalimido)octane
1,4-bis(2-thionaphthalimido)cyclohexane
1,4-bis(2-thionaphthalimido)benzene
1,4-bis(2-thionaphthalimido)nitrobenzene
1,4-bis(2-thionaphthalimido)toluene
1,1-bis(N-thio-4-cyclohexene-1,2-dicarboximido)methane
1,2-bis(N-thio-4-cyclohexane-1,2-dicarboximido)ethane
1,3-bis(N-thio-4-cyclohexene-1,2-dicarboximido)propane
1,2-bis(N-thio-4-cyclohexene-1,2-dicarboximido)isopropane
1,4-bis(N-thio-4-cyclohexene-1,2-dicarboximido)butane
1,3-bis(N-thio-4-cyclohexene-1,2-dicarboximido)-3-isobutane
1,5-bis(N-thio-4-cyclohexene-1,2-dicarboximido)pentane
1,6-bis(N-thio-4-cyclohexene-1,2-dicarboximido)hexane
1,7-bis(N-thio-4-cyclohexene-1,2-dicarboximido)heptane
1,8-bis(N-thio-4-cyclohexene-1,2-dicarboximido)octane
1,4-bis(N-thio-4-cyclohexene-1,2-dicarboximido)cyclohexane
1,4-bis(N-thio-4-cyclohexene-1,2-dicarboximido)benzene
1,4-bis(N-thio-4-cyclohexene-1,2-dicarboximido)nitrobenzene
1,4-bis(N-thio-4-cyclohexene-1,2-dicarboximido)toluene
1,1-bis(N-thio-1,4,5,6,7,7-hexachlorobicyclo[2.2.1]hept-5-ene-2,3-dicarboximido)methane
1,2-bis(N-thio-1,4,5,6,7,7-hexachlorobicyclo[2.2.1]hept-5-ene-2,3-dicarboximido)ethane
1,3-bis(N-thio-1,4,5,6,7,7-hexachlorobicyclo[2.2.1]hept-5-ene-2,3-dicarboximido)propane
1,2-bis(N-thio-1,4,5,6,7,7-hexachlorobicyclo[2.2.1]hept-5-ene-2,3-dicarboximido)isopropane
1,4-bis(N-thio-1,4,5,6,7,7-hexachlorobicyclo[2.2.1]hept-5-ene-2,3-dicarboximido)butane
1,3-bis(N-thio-1,4,5,6,7,7-hexachlorobicyclo[2.2.1]hept-5-ene-2,3-dicarboximido)-3-isobutane
1,5-bis(N-thio-1,4,5,6,7,7-hexachlorobicyclo[2.2.1]hept-5-ene-2,3-dicarboximido)pentane
1,6-bis(N-thio-1,4,5,6,7,7-hexachlorobicyclo[2.2.1]hept-5-ene-2,3-dicarboximido)hexane
1,7-bis(N-thio-1,4,5,6,7,7-hexachlorobicyclo[2.2.1]hept-5-ene-2,3-dicarboximido)heptane
1,8-bis(N-thio-1,4,5,6,7,7-hexachlorobicyclo[2.2.1]hept-5-ene-2,3-dicarboximido)octane
1,4-bis(N-thio-1,4,5,6,7,7-hexachlorobicyclo[2.2.1]hept-5-ene-2,3-dicarboximido)cyclohexane
1,4-bis(N-thio-1,4,5,6,7,7-hexachlorobicyclo[2.2.1]hept-5-ene-2,3-dicarboximido)benzene
1,4-bis(N-thio-1,4,5,6,7,7-hexachlorobicyclo[2.2.1]hept-5-ene-2,3-dicarboximido)nitrobenzene
1,4-bis(N-thio-1,4,5,6,7,7-hexachlorobicyclo[2.2.1]hept-5-ene-2,3-dicarboximido)toluene
1,3-bis(2-thiophthalimido)-3-isobutane
1,5-bis(2-thiophthalimido)pentane
1,6-bis(2-thiophthalimido)hexane
1,7-bis(2-thiophthalimido)heptane
1,8-bis(2-thiophthalimido)octane
1,4-bis(2-thiophthalimido)cyclohexane
1,4-bis(2-thiophthalimido)benzene
1,4-bis(2-thiophthalimido)nitrobenzene
1,4-bis(2-thiophthalimido)toluene
1,1-bis(2-thiosuccinimido)methane
1,2-bis(2-thiosuccinimido)ethane
1,3-bis(2-thiosuccinimido)propane
1,2-bis(2-thiosuccinimido)isopropane
1,4-bis(2-thiosuccinimido)butane 1,3-bis(2-thiosuccinimido)-3-isobutane, and
1,5-bis(2-thiosuccinimido)pentane.

Rubber stocks containing delayed action accelerators can be used in the process of this invention. Cheaper, more scorchy accelerators can also be used with an excellent degree of improvement. The improved vulcanizing process of this invention can be used advantageously to process stocks containing furnace blacks as well as stocks containing other types of blacks and fillers used in rubber compounding. The invention is also applicable to gum stocks.

Our invention is applicable to rubber mixes containing sulfur-vulcanizing agents, organic accelerators for vulcanization, and antidegradants. For the purposes of this invention, sulfur-vulcanizing agent means elemental sulfur or sulfur-containing vulcanizing agent, for example, an amine disulfide or a polymeric polysulfide. The invention is applicable to vulcanization accelerators of various classes. For example, rubber mixes containing the aromatic thiazole accelerators which include benzothiazyl-2-monocyclohexyl sulfenamide, 2-mercaptobenzothiazole, N-tert-butyl-2-benzothiazole sulfenamide, 2-benzothiazolyl diethyldithiocarbamate, and 2-(morpholinothio)benzothiazole can be used. Amine salts of mercaptobenzothiazole accelerators, for example, the t-butyl amine salt of mercaptobenzothiazole, like salts of morpholine and 2,6-dimethyl morpholine, can be used in the invention. Thiazole accelerators other than aromatic can be used. Stocks containing accelerators, for example, the tetramethylthiuram disulfide, tetramethylthiuram monosulfide, aldehyde amine condensation products, thiocarbamylsulfenamides, thioureas, xanthates, and guanidine derivatives, are substantially improved using the process of our invention. Examples of thiocarbamylsulfenamide accelerators are shown in U.S. Pat. Nos. 2,381,392, Smith assigned to Firestone; 2,388,236, Cooper assigned to Monsanto; 2,424,921, Smith assigned to Firestone; and British Pat. No. 880,912, Dadson assigned to Imperial Chemical Industries Limited. The invention is applicable to accelerator mixtures. The invention is applicable to stocks containing amine antidegradants. Rubber mixes containing antidegradants, for example, N-1,3-dimethylbutyl-N'-phenyl-p-phenylenediamine, N,N'-bis(1,4-dimethylpentyl)-p-phenylenediamine, and other phenylenediamines, ketone, ether, and hydroxy antidegradants and mixtures thereof, are substantially improved using the process of our invention. Mixtures of antidegradants, for example, a mixture of N-1,3-dimethylbutyl-N'-phenyl-p-phenylenediamine and N,N'-bis(1,4-dimethylpentyl)-p-phenylenediamine, furnish a much improved final product when used with the inhibitors of this invention.

The inhibitors of our invention can be used in natural and synthetic rubbers and mixtures thereof. Synthetic rubbers that can be improved by the process of this invention include cis-4-polybutadiene, butyl rubber, ethylene-propylene terpolymers, polymers of 1,3-butadiene, for example 1,3-butadiene itself or isoprene, copolymers of 1,3-butadiene with other monomers, for example styrene, acrylonitrile, and isobutylene, and methyl methacrylate. The invention relates to diene rubbers, and the terms rubber and diene rubber are synonymous for the purpose of this invention.

EXTENDED SUMMARY OF THE INVENTION

Compounds containing the characteristic nucleus

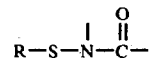

include other valuable compounds besides those in which the dangling valence on the nitrogen is linked to a second carbonyl. The invention also pertains to compounds wherein said valence is linked to alkyl, aryl, cycloalkyl, hydrogen, alkylene carbon or arylene carbon. The second valence of an alkylene radical may directy satisfy the dangling valence on the carbonyl but an arylene radical is usualy linked indirectly to the carbonyl, for example through nitrogen, oxygen, sulfur or an alkylene bridge. Moreover, R may be tri or tetravalent as well as divalent so that the new compounds may in general be represented by the formula

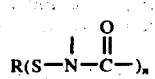

where $n$ is 2, 3 or 4 and R is bridging moiety which is preferably hydrocarbon. However, where R is alkylene the chain may be interrupted by oxygen or sulfur. Similarly, where the bridging moiety comprises more than one arylene, the arylenes may be joined by oxygen or sulfur and such equivalents will be understood to be included by alkylene and arylene. It will also be understood that arylene includes radicals substituted by lower alkyl ad lower alkoxy of 1 to 5 carbon atoms, nitro or chlorine. Illustrative of R where $n$ is 2 are divalent radicals derived by removal of two hydrogen atoms from methane, propane, cyclohexane, isopropane, butane, isobutane, pentane, hexane, heptane, octane, benzene, toluene, diphenyl or from each methyl of xylene (phenylenedimethylene) herein regarded as alkylene. Tri and tetravalent bridging moieties are conveniently derived from esters of mercapto lower fatty acids and di, tri or tetrahydric alcohol. The number of carbon atoms in R is essentially a matter of choice and R may comprise at least 1–24 carbon atoms. For example, R is selected from the group consisting of radical from removing $n$ hydrogens from alkane of 1 to 23 carbon atoms, radical from removing $n$ hydrogens from cycloalkane of 5–15 carbon atoms and radical from removing $n-1$ hydrogens from aryl of 6–12 carbon atoms.

The compounds are conveniently derived from intermediates containing the nucleus

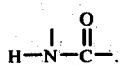

Where the dangling valences are satisfied by the same radical, the intermediates are of course cyclic. Thus, the invention comprises compounds of the formula

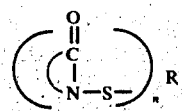

wherein

is a radical derived by removal of hydrogen from an imide of a dicarboxylic acid, from a monocarbonyl cyclic urea, from an imide in which nitrogen is linked to carbonyl by alkylene and from a monocarbonyl azole containing one other different hetero atom in the ring. Representative examples are phthalimido
succinimido
adipimido
glutarimido
3,3-dimethylglutarimido
hexahydrophthalimido
7-oxabicyclo[2.2.1]heptane-2,3-dicarboximido
7-oxabicyclo[2.2.1]hept-5-ene-2,3-dicarboximido
tetrapropenylsuccinimido
methylsuccinimido
octadecylsuccinimido
n-decenylsuccinimido
1,4,5,6,7,7-hexachlorobicyclo[2.2.1]hep-5-ene-2,3-dicarboximido
5,5-dimethyl-3-hydantoinyl
hydantoinyl
5,5-diphenyl-3-hydantoinyl
maleimido
4-cyclohexene-1,2-dicarboximido
2-benzimidazolinon-1-yl
2-benzothiazolinon-N-yl
3-arylthio-2-benzimidazolinon-1-yl
3-alkylthio-2-benzimidazolinon-1-yl
3-cycloalkylthio-2-benzimidazolinon-1-yl
2-imidazolinon-1-yl
3-cycloalkylthio-2-imidazolinon-1-yl
3-arylthio-2-imidazolinon-1-yl
3-alkylthio-2-imidazolinon-1-yl
2-imidazolinon-1-yl
3-cycloalkylthio-2-imidazolidinon-1-yl
3-arylthio-2-imidazolidinon-1-yl
3-alkylthio-2-imidazolidinon-1-yl
bicyclo[2.2.1]hept-5-ene-2,3-dicarboximido
alkylbicyclo[2.2.1]hept-5-ene-2,3-dicarboximido
N-(arylthio)-1,2,4,5-benzenetetracarboxylic-1,2:4,5-diimido
N-(cycloalkylthio)-1,2,4,5-benzenetetracarboxylic-1,2:4,5-diimido
N-(alkylthio)-1,2,4,5-benzenetetracarboxylic-1,2:4,5-diimido naphthalimido
3,4,5,6-tetrahalophthalimido
cyclobutane-1,2-dicarboximido
citraconimido
glutaconimido
caronimido
camphorimido
hydrochelidonimido, and diphenimido.

Where the aforesaid radical is derived from an imide in which nitrogen is linked to carbonyl by alkylene, suitable imides are 2-piperidone, 2-pyrrolidinone, 2(2H)-hexahydroazepinone, 5-methyl-2-pyrrolidinone, 2(1H)hexahydroazocinone, 2(2H)-octahydroazoninone, 2-azacycloundecanone and 2-azacyclododecanone.

A sub-class of the new compounds derived from acyclic intermediates is represented by the formula

where R is the same di, tri or tetravalent moiety as before, n is the valence of R, Y is hydrogen, lower alkyl, aryl or cycloalkyl. Lower alkyl radicals contain 1–5 carbon atoms in the chain which may be optionally substituted by phenyl. Examples of lower alkyl are methyl, ethyl, propyl, isopropyl, butyl, amyl, benzyl, and phenethyl. Examples of aryl are phenyl, tolyl, ethylphenyl and xylyl. Examples of cycloalkyl are cyclopentyl, cyclohexyl, cyclooctyl and methylcyclohexyl. The moiety

constitutes a radical, for example, N-(arylthio)carbamoyl, N-(cycloalkylthio)carbamoyl, N-(alkylthio)carbamoyl, N-arylcarbamoyl, N-alkylcarbamoyl, and N-cycloalkylcarbamoyl.

More particularly, representative examples of

are
N-(phenylthio)carbamoyl
N-(chlorophenylthio)carbamoyl
N-(benzylthio)carbamoyl
N-(tolylthio)carbamoyl
N-(methylthio)carbamoyl
N-(ethylthio)carbamoyl
N-(propylthio)carbamoyl
N-(isopropylthio)carbamoyl
N-(t-butylthio)carbamoyl
N-(dodecylthio)carbamoyl
N-(cyclopentylthio)carbamoyl
N-(cyclohexylthio)carbamoyl
N-(cyclooctylthio)carbamoyl
N-phenylcarbamoyl
N-methylcarbamoyl
N-ethylcarbamoyl
N-propylcarbamoyl
N-isopropylcarbamoyl
N-t-butylcarbamoyl
N-trichloromethylcarbamoyl
N-benzylcarbamoyl
N-nitrophenylcarbamoyl
N-chlorophenylcarbamoyl
N-tolylcarbamoyl
N-dodecylcarbamoyl
N-cyclopentylcarbamoyl
N-cyclohexylcarbamoyl, and
N-cyclooctylcarbamoyl A third sub-class is represented by the formula

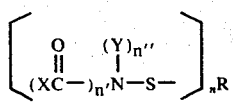

where Y, R and $n$ have the same meaning as before, $n'$ is one or 2 and $n''$ is zero or 1, the sum of $n'$ and $n''$ being two and X is alkyl, cycloalkyl or aryl. Representative examples of

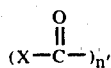

are acetyl, benzoyl, toluoyl, diacetyl, propionyl, butyryl and valeryl.

INTERMEDIATES AND PREPARATION OF THE COMPOUNDS

The compounds of this invention are prepared according to the following equations:

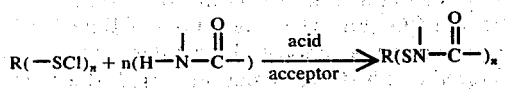

When preparing compounds wherein $n$ is 3 or 4, trithiols or tetrathiols are used as intermediates, examples of which are: 1,2,3-propanetrithiol, 1,2,3-benzenetrithiol, 1,3,5-benzenetrithiol, 1,2,3,4-butanetetrathiol, neopentanetetrathiol, trimethylolethanetri(3-mercaptopropionate), $CH_3C(CH_2OOCCH_2CH_2-SH)_3$, trimethylolethanetrithioglycolate, $CH_3C(CH_2OOCCH_2-SH)_3$, trimethylolpropanetri(3-mercaptopropionate), $CH_3CH_2C(CH_2OOCCH_2CH_2-SH)_3$, trimethylolpropanetrithioglycolate, $CH_3CH_2C(CH_2OOCCH_2-SH)_3$, pentaerythritol tetra(3-mercaptopropionate), $C(CH_2OOCCH_2CH_2-SH)_4$, and pentaerytritol tetrathioglycolate, $C(CH_2OOCCH_2-SH)_4$.

Examples of dithiol reactants suitable as intermediates in the above equation are:

1,1-methanedithiol
1,2-ethanedithiol
phenyl 1,2-ethanedithiol
1,3-propanedithiol
1,2-isopropanedithiol
2,2-propanedithiol
1,2-propanedithiol
2-sec-butyl-2-methyl-1,3-propanedithiol
1,3-diphenyl-2,2-propanedithiol
1,4-butanedithiol
2,3-butanedithiol
1,3-isobutanedithiol
1,5-pentanedithiol
1,6-hexanedithiol
1,2-hexanedithiol
2-ethyl-1,6-hexanedithiol
2,5-dimethyl-3,4-hexanedithiol
2,5-dimethyl-2,4-hexanedithiol
2-ethyl-1,3-hexanedithiol
3,5,5-trimethyl-1,1-hexanedithiol
1,7-heptanedithiol
1,8-octanedithiol
1,2-octanedithiol
2,6-dimethyl-3,7-octanedithiol
2,6-dimethyl-2,6-octanedithiol
1,9-nonanedithiol
1,10-decanedithiol
2,2-camphanedithiol
1,11-undecanedithiol
4,8-dithiaundecane-undecane-1,11-dithiol
1,12-dodecanedithiol
7,8-pentadecanedithiol
1,10-octadecanedithiol
1,12-octadecanedithiol
1,18-octadecanedithiol
12,12-tricosanedithiol
2,2'-oxydiethanethiol
2,2'-thiodiethanethiol
4,4'-oxydibutane-1-thiol
2,2'-(ethylenedithio)diethanethiol, $HSC_2H_4SC_2H_4SC_2H_4SH$
1,1-cyclohexanedimethanethiol
1,2-cyclohexanedimethanethiol
1,4-cyclohexanedimethanethiol
4-mercaptocyclohexaneethanethiol
2-mercaptocyclohexaneethanethiol
3-mercaptocyclohexaneethanethiol
p-benzenediethanethiol
$\alpha,\alpha'$,p-xylenedithiol
2,5-dimethyl-$\alpha,\alpha'$,p-xylenedithiol
$\alpha,\alpha'$-dimethyl-$\alpha,\alpha'$-xylenedithiol
1,1-cyclopentanedithiol
1,2-cyclopentanedithiol
1,1-cyclohexanedithiol
1,2-cyclohexanedithiol
p-menthane-2,9-dithiol
1,1-cycloheptanedithiol
2-methyl-1,1-cyclohexanedithiol
4-tert-butyl-1,1-cyclohexanedithiol
1,1-cyclododecanedithiol
1,1-cyclopentadecanedithiol
9,10-anthracenedimethanethiol
o-benzenedithiol
m-benzenedithiol
4-ethoxy-o-benzenedithiol
5-nitro-m-benzenedithiol
4,5-dimethyl-o-benzenedithiol
p-benzenedithiol
4,5-dimethyl-m-benzenedithiol
2,4-dimethyl-m-benzenedithiol
4-ethyl-m-benzenedithiol
2,5-dichloro-m-benzenedithiol
nitro-p-benzenedithiol
1,4-naphthalenedithiol
1,5-naphthalenedithiol
2,6-naphthalenedithiol
2,7-naphthalenedithiol
1,2,3,4-tetrahydro-2,3-naphthalenedithiol
2,5-toluenedithiol
5-methoxy-2,4-toluenedithiol
3,4-toluenedithiol
2,2'-biphenyldithiol
4,4'-biphenyldithiol
4,4'-oxybisbenzenethiol
glycol dimercaptoacetate, $C_2H_4(OOCCH_2-SH)_2$ and
glycol dimercaptopropionate, $C_2H_4(OOCCH_2CH_2-SH)_2$.

The bis(thioimido)alkanes of this invention derived from imides of dicarboxylic acids are synthesized according to the following equations:

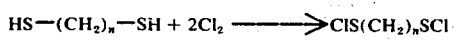

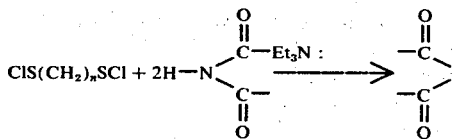

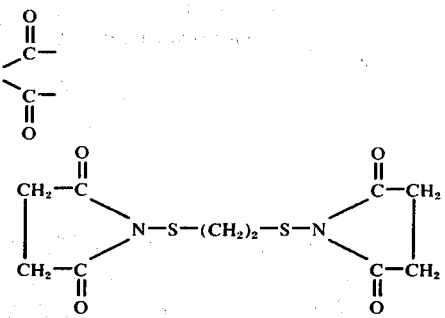

The mercaptan is dissolved in n-pentane and then chlorine gas is passed through the resulting solution at −5° to 5°C. The orange-yellow sulfenyl chloride is added dropwise to a solution of imide and triethylamine in dimethylformamide. The reaction mixture is allowed to stir for 30 minutes and it is then diluted with water. The product is filtered and recrystallized.

To prepare 1,6-bis(2-thiophthalimido)hexane of the formula

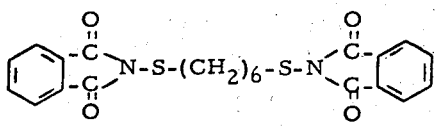

15 grams (0.1 mole) of 1,6-n-hexanedithiol is dissolved in 100 ml. of n-pentane in a 250 ml. round-bottomed three-necked flask equipped with a mechanical stirrer, condenser, a thermometer, and a gas inlet tube. Chlorine gas, 16.0 grams (0.22 mole), is passed through the solution in the flask at −5° to 5°C. over a 20-minute period. The yellow solution of the sulfenyl chloride is added dropwise to a solution of 28 grams (0.2 mole) of phthalimide and 26 grams (0.26 mole) of triethylamine in 150 ml. of dimethylformamide over a period of 30 minutes. The reaction temperature rises 24° to 40°C. upon this addition. The reaction mixture is stirred for 30 minutes and then it is diluted with 2 liters of cold water. The precipitate is filtered and dried. The precipitate weighs 37.5 grams which is an 85% yield. Recrystallization of the product gives a white crystalline 1,6-bis(2-thiophthalimido)hexane with a melting point of 171° to 172°C. Elemental analysis of the 1,6-bis(2-thiophthalimido)hexane shows 6.12% nitrogen and 14.53% sulfur. Calculated percentages for $C_{22}H_{20}N_2O_4S_2$ are 6.36% nitrogen and 14.55% sulfur.

An 89% yield of 1,6-bis(2-thiosuccinimido)hexane is obtained using the synthesis described above. The melting point is 118°–120°C. Elemental analysis of the 1,6-bis(2-thiosuccinimido)hexane shows 7.74% nitrogen and 19.15% sulfur. Calculated percentages for $C_{14}H_{20}N_2O_4S_2$ are 8.13% nitrogen and 18.61% sulfur.

An 85% yield of 1,4-bis(2-thiophthalimido)butane is obtained using the synthesis described above. The melting point is 210°–213°C (decomposes).

To prepare 1,2-bis(2-thiosuccinimido)ethane of the formula 18.8 grams (0.2 mole) of 1,2-ethanedithiol is dissolved in 200 ml. of benzene in a suitable glass reactor. Chlorine gas is passed through the solution at 25°C. until the solution clears. The sulfenyl chloride solution is concentrated by removing 50 ml. of benzene on a rotary evaporator. The sulfenyl chloride solution is added slowly to a solution of 39.6 grams (0.4 mole) of succinimide and 48.4 grams (0.4 mole) of collidine in 500 ml. of benzene over a period of 30 minutes. The precipitate is filtered, washed with water and dried. Recrystallization of the product from dioxane gives substantially pure 1,2-(2-thiosuccinimido)ethane. The melting point is 176°–178°C (decomposes).

1,2-Ethanesulfenyl chloride (0.1 mole) in benzene is added in small portions over a period of one hour to 29.4 grams (0.2 mole) of phthalimide and 30.3 grams (0.3 mole) of triethylamine in 300 ml. of carbon tetrachloride. The mixture is stirred 2 hours and then added to 600 ml. of water. The precipitate is recovered by filtration and dried. 36 Grams of 1,2-bis(2-thiophthalimido)ethane is obtained. Identification is confirmed by nuclear magnetic resonance spectral analysis.

0.2 Mole of 1,2-ethanesulfenyl chloride is added dropwise to solution of caprolactam(2-oxohexamethylenimine) 45.2 g. (0.4 mole) and collidine 48.5 g. (0.4 mole) in 500 ml. of benzene. The solids are collected by filtration and washed with water. 42 Grams of 1,2-bis[2(2H)-hexahydroazepinon-1-ylthio]ethane is recovered. The melting point is 180°–181°C. recrystallized from toluene-heptane. Identification is confirmed by nuclear magnetic resonance spectral analysis.

4.28 Grams of chlorine is added at room temperature to 4.7 grams of 3,4-toluenedithiol in 150 ml. of benzene. The sulfenyl chloride solution is then slowly added to a slurry of 11.2 grams of potassium phthalimide in 100 ml. of dimethylformamide and the mixture stirred for one hour. The reaction mixture is quenched in a liter of water and 3,4-bis(2-thiophthalimido)toluene is recovered by filtration.

The polythiol intermediates used in preparing compounds of this invention may be prepared by hydrolyzing the reaction product of thiourea and the appropriate bromo compound. For example, 1,10-decanedithiol is prepared by adding 100 grams (0.33 mole) of 1,10-dibromodecane to a refluxing solution of 51 grams (0.66 mole) of thiourea in 250 ml. of ethanol. After heating at reflux for 8 hours, a solution of 40 grams sodium hydroxide in 300 ml. of water is added. The solution is heated for two hours during which time an oil layer forms. The oil layer is separated. The alcohol-water solution is acidified with dilute sulfuric acid (7 ml. $H_2SO_4$/50 ml. $H_2O$) to recover additional quantities of dithiol which is combined with the other portion. The crude dithiol is dissolved in benzene, washed with dilute sulfuric acid and dried over sodium sulfate. The benzene is removed by evaporation to give 63.5 grams of 1,10-decanedithiol, a pale yellow liquid, $N_D^{20}$ 1.500.

To prepare, 1,10-bis(2-thiophthalimido)decane, 20.6 grams (0.1 mole) of 1,10-decanedithiol as prepared above is dissolved in 150 ml. of benzene and 14 grams of chlorine gas is added at room temperature. About 30 ml. of the benzene is removed by vacuum stripping. The sulfenyl chloride solution is added dropwise to a slurry of 35.4 grams of potassium phthalimide in 150 ml. of dimethylformamide while cooling the reaction vessel to keep the temperature below 35°C. The reaction mixture is added to 1 liter of water and the resulting precipitate collected by filtration. 45 Grams of substantially pure 1,10-bis(2-thiophthalimido)decane is recovered, a pale cream colored solid which melts at 131°–134°C. when recrystallized from toluene. Nuclear magnetic resonance spectral analysis confirms identification of the product.

Compounds of the formula

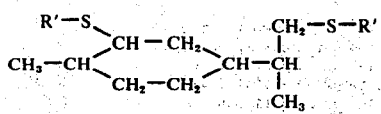

wherein R' is phthalimido, succinimido and 5,5-dimethyl-3-hydantoin are prepared as follows.

Dipentene dimercaptan which is believed to be mainly p-menthane-2,9-dithiol is chlorinated to give p-menthane-2,9-sulfenyl chloride. Potassium phthalimide and p-menthane-2,9-sulfenyl chloride are reacted by following substantially the same procedure described above for preparing 1,10-bis(2-thiophthalimido)decane. 30 Grams of a waxy solid identified as 2,9-bis(2-thiophthalimido)-p-menthane is recovered. p-Menthane-2,9-sulfenyl chloride is reacted with succinimide and triethylamine in dimethylformamide to give 25 grams of a gummy solid identified as 2,9-bis(2-thiosuccinimido)-p-menthane. Similarly, a one molar proportion of 5,5-dimethyl hydantoin is reacted with one molar proportion of p-menthane-2,9-sulfenyl chloride to give a yellow glossy solid identified as 2,9-bis(N-thio-5,5-dimethyl-3-hydantoinyl)-p-menthane.

1,4-Bis(2-thiophthalimido)benzene and 1,4-bis(2-thiosuccinimido)benzene are prepared by reacting p-benzene bis(sulfenyl chloride) with phthalimide or succinimide in the presence of an acid acceptor in an inert solvent and recovering the desired product.

Two molar portions of chlorine are reacted at 0°C with one molar portion of 4,4'-oxybisbenzenethiol to yield 4,4'-oxybis(benzenesulfenyl chloride). The sulfenyl chloride is then added to two molar portions of naphthalimide and triethylamine in dimethyl formamide at room temperature to give 4,4'-bis(2-thionaphthalimido)oxybenzene. Similarly three molar portions of chlorine are reacted with 1,2,3-propanetrithiol and 1,3,5-benzenetrithiol to give the corresponding sulfenyl chlorides. These sulfenyl chlorides are reacted with phthalimide and succinimide to give respectively, 1,2,3-tri(2-thiophthalimido)propane, 1,3,5-tri(2-thiophthalimido)benzene, 1,2,3-tri(2-thiosuccinimido)propane and 1,3,5-tri(2-thiosuccinimido)benzene.

Neopentanetetrathiol is reacted at about 0°C in pentane with four molar portions of chlorine to give the corresponding sulfenyl chloride which is added to potassium hexahydrophthalimide in 200 ml. of benzene. Tetra(N-thiohexahydrophthalimido)neopentane is recovered.

Similarly, chlorine is added to pentaerythritol tetra(-thioglycolate) in hexane at about 0°C. The sulfenyl chloride is added to a solution of phthalimide and triethylamine in dimethyl formamide at room temperature. Pentaerythritol tetra(S-phthalimidothioglycolate) of the formula

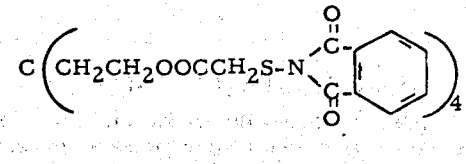

is recovered.

14.2 Grams of chlorine is added to a solution of 24.4 grams of pentaerythritol tetra(3-mercaptopropionate) in about 300 ml. of benzene. The sulfenyl chloride solution is added to 36 grams of potassium phthalimide in 200 ml. of dimethylformamide at room temperature. After stirring one hour, the reaction mixture is added to a liter of water. The product is collected, rinsed with water and dried. Pentaerythritol tetra[3(2-thiophthalimido)propionate] of the formula

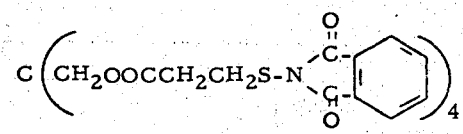

is recovered.

A solution of n-butyl lithium (0.1 mole) in 40 ml. of hexane is added to a slurry of 19.7 g. of benzanilide in 200 ml. of benzene and 50 ml. of tetrahydrofuran at 0°C to yield a red-brown solution of N-lithium benzanilide. 0.05 mole of 1,2-ethane sulfenyl chloride is added to the N-lithium benzanilide solution at 0°C. A white precipitate forms as the sulfenyl chloride is added. The reaction mixture is stirred for 2 hours after which the precipitate is recovered by filtration, washed with water and dried. 23 Grams of 1,2-bis(N-thio-N-phenyl benzamido)ethane is recovered. The melting point recrystallized from toluene is 154°–156°C.

A solution of n-butyl lithium (0.1 mole) in 40 ml. of hexane is added to a solution of 13.5 g. (0.1 mole) of N-methyl benzamide in 200 ml. of benzene and 50 ml. of tetrahydrofuran at 0°C to yield a white gummy precipitate of N-lithium-N-methyl benzamide. 0.05 mole of 1,2-ethane sulfenyl chloride is added to a slurry of N-lithium-N-methyl benzamide at 0°C. A dark gummy precipitate forms as the sulfenyl chloride is added. The solvent is decanted and the residual solvent removed by evaporation to yield a dark brown oil. The oil is dissolved in hot toluene and the toluene removed by evaporation to give 1,2-bis(N-thio-N-methyl benzamido)ethane as a brown tar. Identification is confirmed by nuclear magnetic resonance spectral analysis.

1,2-Ethanesulfenyl chloride (0.1 mole) in benzene is added dropwise to 17.2 g. of 2-imidazolidinone and 20 g. of triethylamine in 150 ml. of dimethylformamide at room temperature. After stirring the mixture about one hour, the mixture is quenched in a liter of water to yield a gummy precipitate. The precipitate which melts after drying at 135°–150°C is recovered by filtration. The product is 1,2-bis(N-thio-2-imidazolidinon-1-yl)ethane mixed with a polymer of the structure

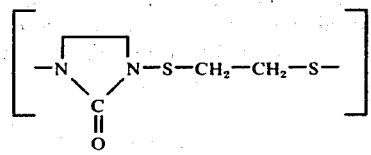

INHIBITING PREVULCANIZATION

The following table illustrates the invention in greater detail and the best mode for carrying it out, but is not to be construed as to narrow the scope of our invention. For the rubber stocks tested and described, infra, as illustrative of the invention, Mooney scorch times at 121°C are determined by means of a Mooney plastometer. The time in minutes ($t_5$) required for the Mooney reading to rise five points above the minimum viscosity is recorded. Longer times are indicative of the activity of the inhibitor. Longer times on the Mooney Scorch Test are desirable because this indicates greater processing safety. Percentage increases in scorch delay are calculated by dividing the Mooney scorch time of the stock containing the premature vulcanization inhibitor by the Mooney scorch time of the control stock, multiplying by 100, and subtracting 100. These increases show the percentage improvement in scorch delay over the control stock which contains no inhibitor. Additionally, curing characteristics are calculated from the time required to cure the stocks at 144°C by means of the Monsanto Oscillating Disk Rheometer which is described by Decker, Wise, and Guerry in Rubber World, December 1962, page 68. From the Rheometer data, R.M.T. is the maximum torque in Rheometer units, $t_2$ is the time in minutes for a rise of two Rheometer units above the minimum reading of the rubber sample, and $t_{90}$ is the time required to obtain a torque 90% of the maximum.

The trademarks of some compounds used in the practice of this invention are Santocure MOR and Santoflex 13. Santocure MOR is the accelerator 2-(morpholinothio)benzothiazole. Santoflex 13 is the antidegradant N-1,3-dimethylbutyl-N′-phenyl-p-phenylenediamine.

Table I illustrates the results of using 1,6-bis(2-thiophthalimido)hexane and 1,4-bis(2-thiophthalimido)butane as premature vulcanization inhibitors in stocks of natural rubber containing the antidegradant Santoflex 13 and the accelerator Santocure MOR. From the data of the table it will be noted that 1,6-bis(2-thiophthalimido)hexane and 1,4-bis(2-thiophthalimido)butane are quite active in the presence of the accelerator as premature vulcanization inhibitors.

The ingredients for the table are as follows. The stocks contain:

|  | Parts by Weight |
|---|---|
| Natural rubber | 100 |
| Carbon black | 45 |
| Zinc oxide | 3 |
| Stearic acid | 2 |
| Hydrocarbon softener | 5 |
| Santoflex 13 | 2 |
| Santocure MOR | 0.5 |
| Sulfur | 2.5 |
| Premature vulcanization inhibitor | as indicated |

There are seven stocks in the table and Stock 1 is the control. Stocks 2–7 contain the following concentrations of premature vulcanization inhibitor.

| Stock | Inhibitor | Parts by Weight |
|---|---|---|
| 1 | — | — |
| 2 | 1,6-bis(2-thiophthalimido)hexane | 0.22 |
| 3 | 1,6-bis(2-thiophthalimido)hexane | 0.44 |
| 4 | 1,6-bis(2-thiophthalimido)hexane | 0.88 |
| 5 | 1,4-bis(2-thiophthalimido)butane | 0.24 |
| 6 | 1,4-bis(2-thiophthalimido)butane | 0.48 |
| 7 | 1,4-bis(2-thiophthalimido)butane | 0.96 |

TABLE I

| Stock | 1 | 2 | 3 | 4 | 5 | 6 | 7 |
|---|---|---|---|---|---|---|---|
| Mooney Scorch at 121°C | | | | | | | |
| $t_5$ | 25.3 | 37.4 | 47.5 | 60.8 | 35.2 | 51.0 | 64.8 |
| % Increase in Scorch Delay | — | 48 | 88 | 140 | 39 | 102 | 156 |
| Rheometer at 144°C | | | | | | | |
| $t_2$ | 8.0 | 10.0 | 12.2 | 15.0 | 9.3 | 11.5 | 14.8 |
| $t_{90}$ | 21.5 | 22.5 | 26.3 | 29.5 | 22.6 | 25.2 | 29.5 |
| R.M.T. | 56.5 | 58.6 | 60.4 | 62.0 | 57.5 | 58.0 | 59.0 |
| $k_2$ | 0.183 | 0.183 | 0.173 | 0.173 | 0.173 | 0.187 | 0.183 |

Other prevulcanization inhibitors of the invention are tested in a similar natural rubber stock containing the same ingredients as previously described except 0.5 parts N-tert-butyl-2-benzothiazolesulfenamide is used as accelerator in stocks 1–5 and 0.6 parts in stock 6 in place of Santocure MOR and 2.0 parts of sulfur is used. The inhibitors are tested at 0.5 parts by weight per 100 parts rubber.

| Stock | Inhibitor |
|---|---|
| 1 | 1,2-bis(2-thiosuccinimido)ethane |
| 2 | 1,10-bis(2-thiophthalimido)decane |
| 3 | 2,9-bis(N-thio-5,5-dimethylhydantoinyl)-p-menthane |
| 4 | 2,9-bis(2-thiosuccinimido)-p-menthane |
| 5 | 2,9-bis(2-thiophthalimido)-p-menthane |
| 6 | 1,2-bis(2(2H)hexahydroazepinon-1-ylthio)ethane |

TABLE II

| Stock | 1 | 2 | 3 | 4 | 5 | 6 |
|---|---|---|---|---|---|---|
| Mooney Scorch at 121°C | | | | | | |
| % Increase in Scorch Delay | 44 | 62 | 40 | 39 | 52 | 113 |

Comparable results to those in the above tables illustrating utility are obtained with the inhibitors of this invention which are not illustrated.

Concentration studies show that the inhibitors of this invention are effective in rubber at concentrations of 0.05 to 5.0 parts per hundred. Concentrations from 0.22 to 3.0 parts per hundred are preferred.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A compound of the formula

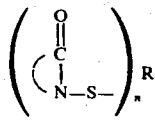

wherein

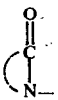

is succinimido, adipimido, glutarimido, 3,3-dimethylglutarimido, tetrapropenylsuccinimido, methylsuccinimido, octadecylsuccinimido, n-decenylsuccinimido, maleimido, citraconimido, glutaconimido, and hydrochelidonimido, $n$ is 2, 3 or 4 equal to the valence of R and R is selected from the group consisting of radical from removing $n$ hydrogens from alkane of 1 to 23 carbon atoms provided when $n$ is 3 or 4 alkane contains at least $n$ carbon atoms, radical from removing $n$ hydrogens from cycloalkane of 5–15 carbon atoms, radical from removing $n-1$ hydrogens from phenyl, naphthyl, or phenyl mono- or di-substituted by lower alkyl, lower alkoxy, nitro or chloro, diphenylene, $C_2H_4(OOCCH_2-)_2$, $C_2H_4(OOCCH_2CH_2-)_2$, $CH_3C(CH_2OOCCH_2-)_3$, $CH_3C(CH_2OOCCH_2-)_3$, $CH_3CH_3C(CH_2OOCCH_2CH_2-)_3$, $CH_3CH_2C(CH_2OOCCH_2-)_3$, $C(CH_2OOCCH_2CH_2-)_4$, and $C(CH_2OOCCH_2-)_4$.

2. The compound of claim 1 in which R is radical from removing $n$ hydrogens from alkane hydrocarbon of 1 to 23 carbon atoms.

3. The compound of claim 1 wherein

is succinimido.

4. The compound of claim 1 wherein

is glutarimido.

5. The compound of claim 3 wherein R is 1,2,3-propane-tri-yl.

6. The compound of claim 1 wherein

is maleimido.

7. The compound of claim 6 wherein R is dimethylene.

8. The compound of claim 3 of the formula

wherein R contains 1 to 8 carbon atoms and R' is succinimido.

9. The compound of claim 8 wherein R is dimethylene.

10. The compound of claim 3 wherein

is succinimido and R is p-menthan-2,9-diyl.

11. The compound of claim 8 wherein R is 1,4-phenylene.

12. The compound of claim 4 wherein R is dimethylene.

* * * * *